United States Patent
Rodrigo et al.

(10) Patent No.: US 10,208,091 B2
(45) Date of Patent: *Feb. 19, 2019

(54) MODIFIED KAPPA LIGHT CHAIN-BINDING POLYPEPTIDES

(71) Applicant: GE HEALTHCARE BIOPROCESS R&D AB, Uppsala (SE)

(72) Inventors: Gustav Rodrigo, Uppsala (SE); Mats Ander, Uppsala (SE); Tomas Bjorkman, Uppsala (SE)

(73) Assignee: GE HEALTHCARE BIOPROCESS R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/526,849

(22) PCT Filed: Dec. 11, 2015

(86) PCT No.: PCT/EP2015/079387
§ 371 (c)(1),
(2) Date: May 15, 2017

(87) PCT Pub. No.: WO2016/096643
PCT Pub. Date: Jun. 23, 2016

(65) Prior Publication Data
US 2017/0327545 A1    Nov. 16, 2017

(30) Foreign Application Priority Data

Dec. 17, 2014 (SE) ...................................... 1451563
Dec. 17, 2014 (SE) ...................................... 1451564

(51) Int. Cl.
| | | |
|---|---|---|
| *C07K 14/195* | (2006.01) | |
| *C07K 1/22* | (2006.01) | |
| *C07K 16/00* | (2006.01) | |

(52) U.S. Cl.
CPC .............. *C07K 14/195* (2013.01); *C07K 1/22* (2013.01); *C07K 16/00* (2013.01); *C07K 2317/55* (2013.01); *C07K 2317/569* (2013.01); *C07K 2319/02* (2013.01)

(58) Field of Classification Search
None
See application file for complete search history.

(56) References Cited

U.S. PATENT DOCUMENTS

| | | | |
|---|---|---|---|
| 6,822,075 B2 | 11/2004 | Bjorck et al. | |
| 6,884,629 B2 | 4/2005 | Gore et al. | |
| 2002/0137918 A1* | 9/2002 | Gore ...................... | C07K 14/33 536/23.53 |
| 2003/0027283 A1 | 2/2003 | Bjorck et al. | |
| 2017/0320919 A1* | 11/2017 | Rodrigo ................ | C07K 14/195 |

FOREIGN PATENT DOCUMENTS

| | | | |
|---|---|---|---|
| EP | 1 114 161 A1 * | 7/2001 | |
| WO | 2005/001480 A1 | 1/2005 | |
| WO | 2005/033130 A2 | 4/2005 | |
| WO | WO 2005/033130 A2 * | 4/2005 | |
| WO | 2005/113584 A1 | 12/2005 | |
| WO | 2008/039141 A1 | 4/2008 | |
| WO | 2014/092636 A1 | 6/2014 | |

OTHER PUBLICATIONS

Enever et al. "Engineering High Affinity Superantigens by Phage Display", J. of Molec. Biol., Academic Press, UK, vol. 347, No. 1, (Mar. 18, 2005), pp. 107-120.*
Bottomley et al. "Cloning, expression and purification of Ppl-1, a kappa-chain binding protein, based upon protein L from Peptostreptococcus magnus", Bioseparation, Kluwer Academic Publishers, Dordrecht, NL, vol. 5, No. 6, (Jan. 1, 1995), pp. 359-367.*
Linhult et al. "Improving the tolerance of a protein a analogue to repeated alkaline exposures using a bypass mutagenesis approach", Proteins: Structure, Function, and Bioinformatics, John Wiley & Sons, Inc., US, vol. 55, No. 2, (May 1, 2004), pp. 407-416.*
Gulich et al. "Engineering *streptococcal* protein G for increased alkaline stability", Protein Engineering, Oxford University Press, Surrey, GB, vol. 15, No. 10, (Oct. 1, 2002), pp. 835-842.*
Palmer et al. "Design of stability at extreme alkaline pH in *streptococcal* protein G", J. of Biotech., Elsevier Science Publ., Amsterdam, NL, vol. 134, No. 3-4, (Apr. 30, 2008), pp. 222-230.*
Gulich et al. "Stability towards alkaline conditions can be engineered into a protein ligand", J. of Biotech., Elsevier Science Publ., Amsterdam, NL, vol. 80, No. 2, (Jun. 23, 2000), pp. 169-178.*
PCT International Search Report and Written Opinion for PCT Application No. PCT/EP2015/079387 dated Apr. 15, 2016 (14 pages).
PCT International-Type Search Report SE Application No. ITS/SE214/00286 dated Jun. 23, 2015 (6 pages).
Enever et al., "Engineering High Affinity Superantigens by Phage Display," Journal of Molecular Biology, 2005, 347(1):107-120.
Bottomley et al., "Cloning, Expression and Purification of PPL-1, A Kappa-Chain Binding Protein, Based upon Protein L from Peptostreptococcus Magnus," Bioseparation, 1995, 5(6):359-367.
Linhult et al., "Improving the Tolerance of a Protein a Analogue to Repeated Alkaline Exposures Using a Bypass Mutagenesis Approach," Proteins:Structure, Function, and Bioinformatics, 2004, 55(2):407-416.
Gulich et al., "Engineering *Streptococcal* Protein G for Increased Alkaline Stability," Protein Engineering, 2002, 15(10):835-842.
Palmer et al., "Design of Stability at Extreme Alkaline pH in *Streptococcal* Protein G," Journal of Biotechnology, 2008, 134(3-4)222-230.
Gulich et al., "Stability Towards Alkaline Conditions Can be Engineering into a Protein Ligand," Journal of Biotechnology, 2000, 80(2):169-178.

(Continued)

*Primary Examiner* — Maury A Audet
(74) *Attorney, Agent, or Firm* — Eversheds Sutherland (US) LLP

(57) ABSTRACT

A kappa light chain-binding polypeptide comprising or consisting essentially of one or more binding domains of *Peptostreptococcus* Protein L, each of said domains being selected from the group consisting of domain 2, domain 3 and domain 4.

13 Claims, 5 Drawing Sheets

Specification includes a Sequence Listing.

(56) References Cited

OTHER PUBLICATIONS

Nilson et al., "Protein L from Peptostreptococcus magnus Binds to the K Light Chain Variable Domain*," the Journal of Biological Chemistry, 1992, 267(4):2234-2239.

Hjerten, "The Preparation of Agarose Spheres for Chromatography of Molecules and Particles," Biochimica et Biophysica Acta, 1964, 79:393-398.

Kastern et al., "Structure of Peptostreptococcal Protein L and Identification of a Repeated Immunoglobulin Light Chain-binding Domain*," The Journal of Biological Chemistry, 1992, 267(18):12820-12825.

Akerstrom et al., "Protein L: An Immunoglobulin Light Chain-binding Bacterial Protein Characterization of Binding and Physicochemical Properties," The Journal of Biological Chemistry, 1989, 264(33):19740-19746.

Capto L from GE Healthcare Bio-Sciences AB, Sweden (Capto L data file 29-0100-08 AC, 2014) (8 pages).

Arshady, "Styrene Based Polymer Supports Developed by Suspension Polymerization," Department of Chemistry, University of Tabriz, Iran (6 pages).

Gel Filtration Principles and Methods, 5th Edition, Pharmacia LKB Biotechnology, 1991 (14 pages).

PCT International-Type Search Report SE Application No. ITS/SE214/00287 dated Jun. 23, 2015 (7 pages).

* cited by examiner

Alignment of Protein L kappa light chain-binding domains

```
1 SEEEVTIKAN LIFANGSTQT AEFKGTFEKA TSEAYAYADT LKKDNGEYTV DVADKGYTLN IKFAGKEKTP EE    72  (SEQ ID NO: 2)
2 PKEEVTIKAN LIYADGKTQT AEFKGTFEEA TAEAYRYADA LKKDNGEYTV DVADKGYTLN IKFAGKEKTP EE    72  (SEQ ID NO: 3)
3 PKEEVTIKAN LIYADGKTQT AEFKGTFEEA TAEAYRYADL LAKENGKYTV DVADKGYTLN IKFAGKEKTP EE    72  (SEQ ID NO: 4)
4 PKEEVTIKAN LIYADGKTQT AEFKGTFAEA TAEAYRYADL LAKENGKYTA DLEDGGYTIN IRFAGKKVDE KPE   73  (SEQ ID NO: 5)
5 EKEQVTIKEN IYFEDGTVQT ATFKGTFAEA TAEAYRYADL LSKEHGKYTA DLEDGGYTIN IRFAG             64  (SEQ ID NO: 6)

Pos        10         20         30         40         50         60         70
```

Fig. 1

MODIFIED KAPPA LIGHT CHAIN-BINDING POLYPEPTIDES

CROSS REFERENCE TO RELATED APPLICATIONS

This application claims the priority benefit of PCT/EP2015/079387 filed on Dec. 11, 2015 which claims priority benefit of Swedish Application No. 1451563-9 filed Dec. 17, 2014. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 8, 2017, is named 39130038_1.txt and is 21,902 bytes in size.

TECHNICAL FIELD OF THE INVENTION

The present invention relates to the field of affinity chromatography, and more specifically to polypeptides comprising kappa light chain-binding domains of Protein L, which are useful in affinity chromatography of many types of immunoglobulins and immunoglobulin fragments. The invention also relates to separation matrices containing the polypeptides and to separation methods using such separation matrices.

BACKGROUND OF THE INVENTION

Immunoglobulins and immunoglobulin fragments represent the most prevalent biopharmaceutical products in either manufacture or development worldwide. The high commercial demand for and hence value of this particular therapeutic market has led to the emphasis being placed on pharmaceutical companies to maximize the productivity of their respective manufacturing processes whilst controlling the associated costs.

Affinity chromatography, typically on matrices comprising staphylococcal Protein A or variants thereof, is normally used as one of the key steps in the purification of intact immunoglobulin molecules. The highly selective binding of Protein A to the Fc chain of immunoglobulins provides for a generic step with very high clearance of impurities and contaminants.

For antibody fragments, such as Fab, single-chain variable fragments (scFv), bi-specific T-cell engagers (BiTEs), domain antibodies etc., which lack the Fc chain but have a subclass 1,3 or 4 kappa light chain, matrices comprising Protein L derived from *Peptostreptococcus magnus* (B Åkerström, L Björck: J. Biol. Chem. 264, 19740-19746, 1989; W Kastern et al: J. Biol. Chem. 267, 12820-12825, 1992; B H K Nilson et al: J. Biol. Chem. 267, 2234-2239, 1992 and U.S. Pat. No. 6,822,075) show great promise as a purification platform providing the high selectivity needed. The Protein L disclosed in U.S. Pat. No. 6,822,075 comprises the amino acid sequence SEQ ID NO: 1 plus an additional AVEN sequence at the N-terminus.

(Protein L)
SEQ ID NO: 1
KEETPETPETD SEEEVTIKAN LIFANGSTQT AEFKGTFEKA

TSEAYAYADT LKKDNGEYTV DVADKGYTLN IKFAGKEKTPEE

PKEEVTIKAN LIYADGKTQT AEFKGTFEEA TAEAYRYADA

LKKDNGEYTV DVADKGYTLN IKFAGKEKTPEE PKEEVTIKAN

LIYADGKTQT AEFKGTFEEA TAEAYRYADL LAKENGKYTV

DVADKGYTLN IKFAGKEKTPEE PKEEVTIKAN LIYADGKTQT

AEFKGTFAEA TAEAYRYADL LAKENGKYTA DLEDGGYTIN

IRFAGKKVDEKPEE

Protein L matrices are commercially available as Capto™ L from GE Healthcare Bio-Sciences AB, Sweden (Capto L data file 29-0100-08 AC, 2014) and can be used for separation of kappa light chain-containing proteins such as intact antibodies, Fab fragments, scFv fragments, domain antibodies etc. About 75% of the antibodies produced by healthy humans have a kappa light chain and many therapeutic monoclonal antibodies and antibody fragments contain kappa light chains.

Any bioprocess chromatography application requires comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used with chromatography media is alkaline solutions that are passed over the matrix. At present the most extensively used cleaning and sanitizing agent is NaOH, and it is desirable to use it in concentrations ranging from 0.05 up to e.g. 1 M, depending on the degree and nature of contamination. Protein L is however a rather alkali-sensitive protein compared to e.g. Protein A and only tolerates up to about 15 mM NaOH over a large number of cycles. This means that additional, less desirable cleaning solutions, e.g. urea or guanidinium salts, may also have to be used in order to ensure sufficient cleaning.

An extensive research has earlier been focused on the development of engineered protein A ligands that exhibit an improved capacity to withstand alkaline pH-values. For example, WO2003/080655A1 discloses that Protein A domains with particular asparagine mutations are considerably more alkali stable than the native protein.

There is thus still a need in this field to obtain a separation matrix containing Protein L-derived ligands having an improved stability towards alkaline cleaning procedures.

SUMMARY OF THE INVENTION

One aspect of the invention is to provide a polypeptide with improved alkaline stability. This is achieved with a polypeptide as defined in claim 1.

One advantage is that the alkaline stability is improved over Protein L and the parental polypeptides. A further advantage is that the highly selective binding towards kappa light chain-containing proteins demonstrated for Protein L is retained in the polypeptides of the invention.

A second aspect of the invention is to provide a nucleic acid or a vector encoding a polypeptide or multimer with improved alkaline stability. This is achieved with a nucleic acid or vector as defined in the claims.

A third aspect of the invention is to provide an expression system capable of expressing a polypeptide or multimer with improved alkaline stability. This is achieved with an expression system as defined in the claims.

A fourth aspect of the invention is to provide a separation matrix capable of selectively binding kappa light chain-containing proteins and exhibiting an improved alkaline stability. This is achieved with a separation matrix as defined in the claims.

A fifth aspect of the invention is to provide an efficient and economical method of isolating a kappa light chain-containing protein. This is achieved with a method as defined in the claims.

Further suitable embodiments of the invention are described in the dependent claims.

DEFINITIONS

The terms "antibody" and "immunoglobulin" are used interchangeably herein, and are understood to include also fragments of antibodies, fusion proteins comprising antibodies or antibody fragments and conjugates comprising antibodies or antibody fragments.

The terms a "kappa light chain-binding polypeptide" and "kappa light chain-binding protein" herein mean a polypeptide or protein respectively, capable of binding to a subclass 1, 3 or 4 kappa light chain of an antibody (also called $V_{\kappa I}$, $V_{\kappa III}$ and $V_{\kappa IV}$, as in B H K Nilson et al: J. Biol. Chem. 267, 2234-2239, 1992), and include e.g. Protein L, and any variant, fragment or fusion protein thereof that has maintained said binding property.

The term "kappa light chain-containing protein" is used as a synonym of "immunoglobulin kappa light chain-containing protein" and herein means a protein comprising a subclass 1, 3 or 4 kappa light chain (also called $V_{\kappa I}$, $V_{\kappa III}$ and $V_{\kappa IV}$, as in B H K Nilson et al: J. Biol. Chem. 267, 2234-2239, 1992) derived from an antibody and includes any intact antibodies, antibody fragments, fusion proteins, conjugates or recombinant proteins containing a subclass 1, 3 or 4 kappa light chain.

BRIEF DESCRIPTION OF FIGURES

FIG. 1 shows an alignment of the five kappa light chain-binding domains of Protein L as described in U.S. Pat. No. 6,822,075 and W Kastern et al: J Biol. Chem. 267, 12820-12825, 1992.

DETAILED DESCRIPTION OF EMBODIMENTS

Figure 2:
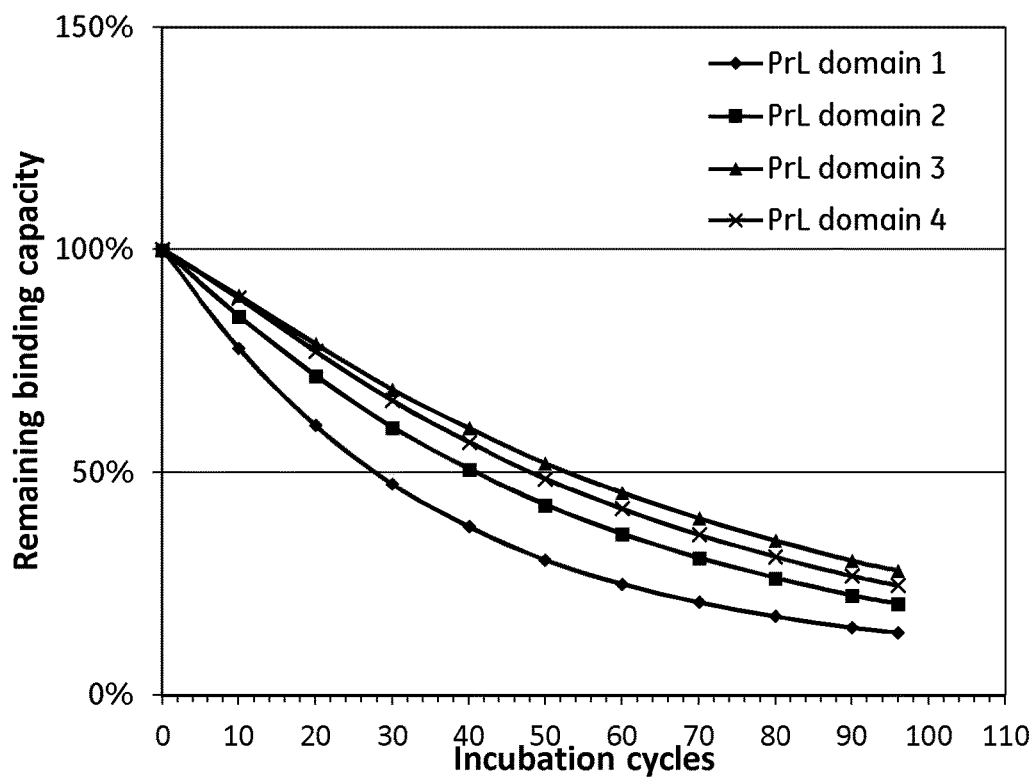
FIG. 2 shows the alkali stability of different kappa light chain-binding domains of Protein L.

In one aspect the present invention discloses a kappa light chain-binding polypeptide comprising or consisting essentially of one or more binding domains of *Peptostreptococcus magnus* Protein L, wherein each of these domains is selected from the group consisting of Domain 2, Domain 3 and Domain 4. Domain 2 can have an amino acid sequence defined by SEQ ID NO:3 or SEQ ID NO:12, or it can have at least 90%, such as at least 95%, sequence homology with SEQ ID NO:3 or 12. SEQ ID NO: 12 is a variant of SEQ ID NO: 3, with an alanine in position 31.

Domain 3 can have an amino acid sequence defined by SEQ ID NO:4, or it can have at least 90%, such as at least 95%, sequence homology with SEQ ID NO:4. Domain 4 can have an amino acid sequence defined by SEQ ID NO:5, or it can have at least 90%, such as at least 95%, sequence homology with SEQ ID NO:5.

In some embodiments of the polypeptide, each domain is selected from the group consisting of Domain 3 and Domain 4, or each of the domains is Domain 3. Specifically, the polypeptide may comprise or consist essentially of a multimer of Domain 3.

In certain embodiments, at least two of the domains are selected from the group consisting of Domain 2, Domain 3 and Domain 4, or from the group consisting of Domain 3 and Domain 4.

In some embodiments, the polypeptide does not contain any Domain 1 of *Peptostreptococcus* Protein L. Domain 1 can have an amino acid sequence as defined by SEQ ID NO:2, or it can have at least 90%, such as at least 95% sequence homology with SEQ ID NO:2.

In certain embodiments of the polypeptide, at least the amino acid at the position corresponding to position 45 in SEQ ID NO:2-5 (e.g. the amino acid at position 45 in SEQ ID NO: 2-5 or 12) in one or more, such as all, of the binding domains has been mutated to an amino acid which is not asparagine, proline or cysteine. The amino acid at position 45 can e.g. be mutated to an alanine.

In some embodiments of the polypeptide, at least the amino acid at the position corresponding to position 10 in SEQ ID NO:2-5 (e.g. the amino acid at position 10 in SEQ ID NO: 2-5 or 12) in one or more, such as all, of the binding domains has been mutated to an amino acid which is not asparagine, proline or cysteine. The amino acid at position 10 can e.g. be mutated to a glutamine.

In certain embodiments of the polypeptide, at least the amino acid at the position corresponding to position 60 in SEQ ID NO:2-5 (e.g. the amino acid at position 60 in SEQ ID NO: 2-5 or 12) in one or more, such as all, of the binding domains has been mutated to an amino acid which is not asparagine, proline or cysteine. The amino acid at position 60 can e.g. be mutated to a glutamine.

Specifically, one or more, such as all, of the binding domains may have mutations selected from the group consisting of N10Q; N45A; N60Q; N10Q,N45A; N45A,N60Q, N10Q,N60Q and N10Q,N45A,N60Q, or alternatively selected from the group consisting of N45A; N10Q,N45A; N45A,N60Q and N10Q,N45A,N60Q.

In some embodiments of the polypeptide, at least the amino acid at the position corresponding to position 19 in SEQ ID NO:2-5 (e.g. the amino acid at position 19 in SEQ ID NO: 2-5 or 12) in one or more, such as all, of the binding domains has been mutated to an amino acid which is not glutamine, asparagine, proline or cysteine. The amino acid at position 19 can e.g. be mutated to a glutamic acid or an alanine. Specifically, one or more, such as all, of the binding domains may have mutations selected from the group consisting of Q19E and Q19A.

In certain embodiments of the polypeptide, one or more, such as all, of said binding domains has an amino acid sequence selected from the group consisting of sequences defined by SEQ ID NO:7, SEQ ID NO:8, SEQ ID NO:9, SEQ ID NO:10, SEQ ID NO:11, SEQ ID NO:13 and SEQ ID NO:14. One or more, such as all, of said binding domains can alternatively have an amino acid sequence selected from the group consisting of sequences defined by SEQ ID NO:7, SEQ ID NO:8, SEQ ID NO:9, SEQ ID NO:10 and SEQ ID NO:11. The polypeptide may further at the N-terminus comprise a plurality of amino acid residues originating from the cloning process or constituting a residue from a cleaved off signaling sequence. The number of additional amino acid residues may e.g. be 15 or less, such as 10 or less or 5 or less. As a specific example, the polypeptide may comprise an AQV sequence at the N-terminus.

(Domain 3, N45A mutation)
SEQ ID NO: 7
PKEEVTIKAN LIYADGKTQT AEFKGTFEEA TAEAYRYADL
LAKEAGKYTV DVADKGYTLN IKFAGKEKTPEE (Domain 3, N10Q, N45A mutation)
SEQ ID NO: 8
PKEEVTIKAQ LIYADGKTQT AEFKGTFEEA TAEAYRYADL
LAKEAGKYTV DVADKGYTLN IKFAGKEKTPEE (Domain 3, N45A, N60Q mutation)
SEQ ID NO: 9
PKEEVTIKAN LIYADGKTQT AEFKGTFEEA TAEAYRYADL
LAKEAGKYTV DVADKGYTLQ IKFAGKEKTPEE (Domain 3, N10Q, N60Q mutation)
SEQ ID NO: 10
PKEEVTIKAQ LIYADGKTQT AEFKGTFEEA TAEAYRYADL
LAKENGKYTV DVADKGYTLQ IKFAGKEKTPEE (Domain 3, N10Q, N45A, N60Q mutation)
SEQ ID NO: 11
PKEEVTIKAQ LIYADGKTQT AEFKGTFEEA TAEAYRYADL
LAKEAGKYTV DVADKGYTLQ IKFAGKEKTPEE (variant of Domain 2)
SEQ ID NO: 12
PKEEVTIKAN LIYADGKTQT AEFKGTFEEA AAEAYRYADA
LKKDNGEYTV DVADKGYTLN IKFAGKEKTPEE (Domain 3, Q19A mutation)
SEQ ID NO: 13
PKEEVTIKAN LIYADGKTAT AEFKGTFEEA TAEAYRYADL
LAKENGKYTV DVADKGYTLN IKFAGKEKTPEE (Domain 3, Q19E mutation)
SEQ ID NO: 14
PKEEVTIKAN LIYADGKTET AEFKGTFEEA TAEAYRYADL
LAKENGKYTV DVADKGYTLN IKFAGKEKTPEE In some embodiments, the polypeptide is a multimer comprising, or consisting essentially of, a plurality of mutated or non-mutated domains as defined by any embodiment disclosed above. The multimer can e.g. be a dimer, a trimer, a tetramer, a pentamer or a hexamer. It can be a homomultimer, where all the units in the multimer are identical or it can be a heteromultimer, where at least one unit differs from the others. Advantageously, all the units in the multimer are alkali stable, such as by comprising the mutations disclosed above. The domains can be linked to each other directly by peptide bonds between the C- and N-termini of the domains. Alternatively, two or more units in the multimer can be linked by elements comprising oligomeric or polymeric species, such as elements comprising up to 15 or 30 amino acids, such as 1-5, 1-10 or 5-10 amino acids. The nature of such a link should preferably not destabilize the spatial conformation of the domains. This can e.g. be achieved by avoiding the presence of cysteine in the links. Furthermore, said link should preferably also be sufficiently stable in alkaline environments not to impair the properties of the domains. For this purpose, it is advantageous if the links do not contain asparagine. It can additionally be advantageous if the links do not contain glutamine. The multimer may further at the N-terminus comprise a plurality of amino acid residues originating from the cloning process or constituting a residue from a cleaved off signaling sequence. The number of additional amino acid residues may e.g. be 15 or less, such as 10 or less or 5 or less. As a specific example, the multimer may comprise an AQV sequence at the N-terminus.

In certain embodiments, the multimer may comprise, or consist essentially, of a sequence selected from the group consisting of: SEQ ID NO: 15, SEQ ID NO: 16, SEQ ID NO: 17 and SEQ ID NO: 18, such as a sequence selected from the group consisting of SEQ ID NO: 16, SEQ ID NO: 17 and SEQ ID NO: 18.

(Domain 3, tetramer)
SEQ ID NO: 15
PKEEVTIKAN LIYADGKTQT AEFKGTFEEA TAEAYRYADL

LAKENGKYTV DVADKGYTLN IKFAGKEKTPEE PKEEVTIKAN

LIYADGKTQT AEFKGTFEEA TAEAYRYADL LAKENGKYTV

DVADKGYTLN IKFAGKEKTPEE PKEEVTIKAN LIYADGKTQT

AEFKGTFEEA TAEAYRYADL LAKENGKYTV DVADKGYTLN

IKFAGKEKTPEE PKEEVTIKAN LIYADGKTQT AEFKGTFEEA

TAEAYRYADL LAKENGKYTV DVADKGYTLN IKFAGKEKTPEE

Domain 3(N10Q, N45A, N60Q)2
SEQ ID NO: 16
PKEEVTIKAQ LIYADGKTQT AEFKGTFEEA TAEAYRYADL

LAKEAGKYTV DVADKGYTLQ IKFAGKEKTPEE PKEEVTIKAQ

LIYADGKTQT AEFKGTFEEA TAEAYRYADL LAKEAGKYTV

DVADKGYTLQ IKFAGKEKTPEE

Domain 3 (N10Q, N45A, N60Q)4
SEQ ID NO: 17
PKEEVTIKAQ LIYADGKTQT AEFKGTFEEA TAEAYRYADL

LAKEAGKYTV DVADKGYTLQ IKFAGKEKTPEE PKEEVTIKAQ

LIYADGKTQT AEFKGTFEEA TAEAYRYADL LAKEAGKYTV

DVADKGYTLQ IKFAGKEKTPEE PKEEVTIKAQ LIYADGKTQT

AEFKGTFEEA TAEAYRYADL LAKEAGKYTV DVADKGYTLQ

IKFAGKEKTPEE PKEEVTIKAQ LIYADGKTQT AEFKGTFEEA

TAEAYRYADL LAKEAGKYTV DVADKGYTLQ IKFAGKEKTPEE

Domain 3 (N10Q, N45A, N60Q)6
SEQ ID NO: 18
PKEEVTIKAQ LIYADGKTQT AEFKGTFEEA TAEAYRYADL

LAKEAGKYTV DVADKGYTLQ IKFAGKEKTPEE PKEEVTIKAQ

LIYADGKTQT AEFKGTFEEA TAEAYRYADL LAKEAGKYTV

DVADKGYTLQ IKFAGKEKTPEE PKEEVTIKAQ LIYADGKTQT

AEFKGTFEEA TAEAYRYADL LAKEAGKYTV DVADKGYTLQ

IKFAGKEKTPEE PKEEVTIKAQ LIYADGKTQT AEFKGTFEEA

TAEAYRYADL LAKEAGKYTV DVADKGYTLQ IKFAGKEKTPEE

PKEEVTIKAQ LIYADGKTQT AEFKGTFEEA TAEAYRYADL

LAKEAGKYTV DVADKGYTLQ IKFAGKEKTPEE PKEEVTIKAQ

```
LIYADGKTQT AEFKGTFEEA TAEAYRYADL LAKEAGKYTV

DVADKGYTLQ IKFAGKEKTPEE
```

In some embodiments, the polypeptide and/or multimer, as disclosed above, further comprises at the C-terminus or N-terminus one or more coupling elements, selected from the group consisting of a cysteine residue, a plurality of lysine residues and a plurality of histidine residues. The coupling element may e.g. be a single cysteine at the C-terminus. The coupling element(s) may be directly linked to the C- or N-terminus, or it/they may be linked via a linker comprising up to 15 amino acids, such as 1-5, 1-10 or 5-10 amino acids. This stretch should preferably also be sufficiently stable in alkaline environments not to impair the properties of the mutated protein. For this purpose, it is advantageous if the stretch does not contain asparagine. It can additionally be advantageous if the stretch does not contain glutamine. An advantage of having a C- or N-terminal cysteine is that endpoint coupling of the protein can be achieved through reaction of the cysteine thiol with an electrophilic group on a support. This provides excellent mobility of the coupled protein which is important for the binding capacity.

The alkali stability of the polypeptide or multimer can be assessed by coupling it to an SPR chip, e.g. to Biacore CM5 sensor chips as described in the examples, and measuring the kappa light chain-binding capacity of the chip, using e.g. a specific kappa light chain-containing protein or polyclonal human IgG (where the majority of the IgG molecules have a kappa light chain), before and after incubation in alkaline solutions at a specified temperature, e.g. 22+/−2° C. The incubation can e.g. be performed in 0.1 M NaOH for a number of 10 min cycles, such as 50, 96 or 100 cycles. The binding capacity of the matrix after 96-100 10 min incubation cycles in 0.1 M NaOH at 22+/−2° C. can be at least 40, such as at least 50, or at least 55% of the binding capacity before the incubation. Alternatively, the remaining binding capacity after 96-100 cycles for a particular mutant measured as above can be compared with the remaining binding capacity for the parental polypeptide/multimer. In this case, the remaining binding capacity for the mutant may be at least 105%, such as at least 110%, at least 125%, at least 150% or at least 200% of the parental polypeptide/multimer.

The invention also discloses a kappa light chain-binding polypeptide comprising at least one mutated binding domain of *Peptostreptococcus* Protein L, in which at least one asparagine residue of a parental domain defined by, or having at least 95% or 98% sequence homology with, SEQ ID NO: 2-6 or 12 has been mutated to another amino acid residue which is not asparagine, proline or cysteine. The polypeptide may comprise at least the mutation N45A and/or the mutation N60Q. In specific embodiments, the mutation(s) are selected from the group consisting of N45A; N10Q,N45A; N45A,N60Q, N10Q,N60Q and N10Q,N45A, N60Q, or alternatively selected from the group consisting of N45A; N10Q,N45A; N45A,N60Q and N10Q,N45A,N60Q. The alkali stability relative to a parental polypeptide can be improved and measured as disclosed above.

In some embodiments the polypeptide comprises or consists essentially of a plurality of mutated binding domains, such as 2, 3, 4, 5 or 6 domains, wherein each domain comprises at least one of the mutations N10Q, N45A and N60Q, such as N45A and/or N60Q. Specifically, the mutation(s) in each domain can be selected from the group consisting of N45A; N10Q,N45A; N45A,N60Q, N10Q, N60Q and N10Q,N45A,N60Q, or alternatively selected from the group consisting of N45A; N10Q,N45A; N45A, N60Q and N10Q,N45A,N60Q. The domains can optionally be linked to each other by elements comprising up to 15 amino acids.

In a second aspect the present invention discloses a nucleic acid encoding a polypeptide or multimer according to any embodiment disclosed above. Thus, the invention encompasses all forms of the present nucleic acid sequence such as the RNA and the DNA encoding the polypeptide or multimer. The invention embraces a vector, such as a plasmid, which in addition to the coding sequence comprises the required signal sequences for expression of the polypeptide or multimer according the invention. In one embodiment, the vector comprises nucleic acid encoding a multimer according to the invention, wherein the separate nucleic acids encoding each unit may have homologous or heterologous DNA sequences.

In a third aspect the present invention discloses an expression system, which comprises, a nucleic acid or a vector as disclosed above. The expression system may e.g. be a gram-positive or gram-negative prokaryotic host cell system, e.g. *Bacillus* sp. or *Escherichia coli* which has been modified to express the present polypeptide or multimer. In an alternative embodiment, the expression system is a eukaryotic host cell system, such as a yeast, e.g. *Pichea pastoris* or *Saccharomyces cerevisiae*.

In a fourth aspect, the present invention discloses a separation matrix, wherein a plurality of polypeptides or multimers according to any embodiment disclosed above have been coupled to a solid support. Such a matrix is useful for separation of kappa light chain-containing proteins and, due to the improved alkali stability of the polypeptides/multimers, the matrix will withstand highly alkaline conditions during cleaning, which is essential for long-term repeated use in a bioprocess separation setting. The alkali stability of the matrix can be assessed by measuring the kappa light chain-binding capacity, using e.g. a specific kappa light chain-containing protein or polyclonal human IgG, before and after incubation in alkaline solutions at a specified temperature, e.g. 22+/−2° C. The incubation can e.g. be performed in 0.1 M NaOH for a number of 15 min cycles, such as 100, 200 or 300 cycles. The binding capacity of the matrix after 100 15 min incubation cycles in 0.1 M NaOH at 22+/−2° C. can be at least 80, such as at least 85, at least 90 or at least 95% of the binding capacity before the incubation. Alternatively, the incubation can be performed in 0.1 M NaOH for a number of 4 h cycles, such as 6 cycles giving a total incubation time of 24 h. The binding capacity of the matrix after 24 h min total incubation time in 0.1 M NaOH at 22+/−2° C. can be at least 80, such as at least 85, at least 90 or at least 95% of the binding capacity before the incubation.

As the skilled person will understand, the expressed polypeptide or multimer should be purified to an appropriate extent before been immobilized to a support. Such purification methods are well known in the field, and the immobilization of protein-based ligands to supports is easily carried out using standard methods. Suitable methods and supports will be discussed below in more detail.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. The solid support can suitably be porous. The porosity can be expressed as a Kav or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. By definition, both Kd and Kav values always lie within the range 0-1. The Kav value can advantageously be 0.6-0.95, e.g. 0.7-0.90 or 0.6-0.8, as measured with dextran of Mw 110 kDa as a probe molecule. An advantage of this is that the support has a large fraction of pores able to accommodate both the polypeptides/multimers of the invention and immunoglobulins binding to the polypeptides/multimers and to provide mass transport of the immunoglobulins to and from the binding sites.

The polypeptides or multimers may be attached to the support via conventional coupling techniques utilising e.g. thiol, amino and/or carboxy groups present in the ligand. Bisepoxides, epichlorohydrin, CNBr, N-hydroxysuccinimide (NHS) etc. are well-known coupling reagents. Between the support and the polypeptide/multimer, a molecule known as a spacer can be introduced, which improves the availability of the polypeptide/multimer and facilitates the chemical coupling of the polypeptide/multimer to the support. Suitable spacers can be introduced e.g. by activation of the support with epichlorohydrin, butanediol diepoxide, allyl glycidyl ether etc. Alternatively, the polypeptide/multimer may be attached to the support by non-covalent bonding, such as physical adsorption or biospecific adsorption.

In some embodiments the matrix comprises 5-20, such as 5-15 mg/ml, 5-11 mg/ml or 8-11 mg/ml of the polypeptide or multimer coupled to the support. The amount of coupled polypeptide/multimer can be controlled by the concentration of polypeptide/multimer used in the coupling process, by the coupling conditions used and/or by the pore structure of the support used. As a general rule the absolute binding capacity of the matrix increases with the amount of coupled polypeptide/multimer, at least up to a point where the pores become significantly constricted by the coupled polypeptide/multimer. The relative binding capacity per mg coupled polypeptide/multimer will decrease at high coupling levels, resulting in a cost-benefit optimum within the ranges specified above.

In some embodiments the polypeptides are coupled to the support via multipoint attachment. This can suitably be done by using such coupling conditions that a plurality of reactive groups in the polypeptide react with reactive groups in the support. Typically, multipoint attachment can involve the reaction of several intrinsic reactive groups of amino acid residues in the sequence, such as amines in lysines, with the reactive groups on the support, such as epoxides, cyanate esters (e.g. from CNBr activation), succinimidyl esters (e.g. from NHS activation) etc. It is however also possible to deliberately introduce reactive groups at different positions in the polypeptides to affect the coupling characteristics. In order to provide multipoint coupling via lysines, the coupling reaction is suitably carried out at a pH where a significant fraction of the lysine primary amines are in the non-protonated nucleophilic state, e.g. at pH higher than 8.0, such as above 10.

In certain embodiments the polypeptides or multimers are coupled to the support via thioether bonds. Methods for performing such coupling are well-known in this field and easily performed by the skilled person in this field using standard techniques and equipment. Thioether bonds are flexible and stable and generally suited for use in affinity chromatography. In particular when the thioether bond is via a terminal or near-terminal cysteine residue on the polypeptide or multimer, the mobility of the coupled polypeptide/multimer is enhanced which provides improved binding capacity and binding kinetics. In some embodiments the polypeptide/multimer is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling. The polypeptide/multimer can e.g. be coupled via single-point attachment, e.g. via a single cysteine or by directed multipoint attachment, using e.g. a plurality of lysines or other coupling groups near a terminus of the polypeptide/multimer.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in the present invention can easily be prepared according to standard methods, such as inverse suspension gelation (S Hjertén: Biochim Biophys Acta 79(2), 393-398 (1964). Alternatively, the base matrices are commercially available products, such as crosslinked agarose beads sold under the name of SEPHAROSE™ FF (GE Healthcare). In an embodiment, which is especially advantageous for large-scale separations, the support has been adapted to increase its rigidity using the methods described in U.S. Pat. No. 6,602,990 or U.S. Pat. No. 7,396,467, which are hereby incorporated by reference in their entirety, and hence renders the matrix more suitable for high flow rates.

In certain embodiments the support, such as a polysaccharide or agarose support, is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to the invention comprises a support of inorganic nature, e.g. silica, zirconium oxide etc.

In yet another embodiment, the solid support is in another form such as a surface, a chip, capillaries, or a filter (e.g. a membrane or a depth filter matrix).

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

In a sixth aspect, the present invention discloses a method of isolating a kappa light chain-containing protein, wherein a separation matrix as disclosed above is used.

In certain embodiments, the method comprises the steps of:
 a) contacting a liquid sample comprising a kappa light chain-containing protein with a separation matrix as disclosed above,
 b) washing said separation matrix with a washing liquid,
 c) eluting the kappa light chain-containing protein from the separation matrix with an elution liquid, and
 d) cleaning the separation matrix with a cleaning liquid.

The method may also comprise steps of, before step a), providing an affinity separation matrix according to any of the embodiments described above and providing a solution comprising a kappa light chain-containing protein and at least one other substance as a liquid sample and of, after step c), recovering the eluate and optionally subjecting the eluate to further separation steps, e.g. by anion or cation exchange chromatography, multimodal chromatography and/or hydrophobic interaction chromatography. Suitable compositions of the liquid sample, the washing liquid and the elution liquid, as well as the general conditions for performing the separation are well known in the art of affinity chromatography and in particular in the art of Protein L chromatography. The liquid sample comprising a kappa light chain-containing protein and at least one other substance may comprise host cell proteins (HCP), such as chinese hamster ovary (CHO) cell, $E.\ coli$ or yeast cell proteins. Contents of CHO cell and $E.\ coli$ proteins can conveniently be determined by immunoassays directed towards these proteins, e.g. the CHO HCP or $E.\ coli$ HCP ELISA kits from Cygnus Technologies. The host cell proteins or CHO cell/$E.\ coli$/yeast proteins may be desorbed during step b).

The elution may be performed by using any suitable solution used for elution from Protein L media. This can e.g. be a solution or buffer with pH 4 or lower, such as pH 2.5-4 or 2.8-3.5.

In some embodiments the elution buffer or the elution buffer gradient comprises at least one mono- di- or trifunctional carboxylic acid or salt of such a carboxylic acid. In certain embodiments the elution buffer or the elution buffer gradient comprises at least one anion species selected from the group consisting of acetate, citrate, glycine, succinate, phosphate, and formiate.

In some embodiments, the cleaning liquid is alkaline, such as with a pH of 12-14. Such solutions provide efficient cleaning of the matrix, in particular at the upper end of the interval In certain embodiments, the cleaning liquid comprises 0.01-1.0 M NaOH or KOH, such as 0.05-1.0 or 0.05-0.1 M NaOH or KOH. The high stability of the polypeptides of the invention enables the use of such comparatively strong alkaline solutions.

In some embodiments, steps a)-d) are repeated at least 10 times, such as at least 50 times or 50-200 times. This is important for the process economy in that the matrix can be re-used many times.

EXAMPLES

Mutagenesis of Protein

Monomer constructs were designed from a Protein L disclosed in U.S. Pat. No. 6,822,075 (SEQ ID NO: 1), containing four kappa light chain-binding domains. These are numbered 1, 2, 3 and 4, starting from the N-terminus (FIG. 1). The DNA fragments were purchased from a DNA synthesizing company (DNA2.0). Four monomer constructs were prepared in a pJexpress201 cloning vector, each with an N-terminal cysteine. For an overview of constructs, see SEQ ID NO: 2,4,5,12. Constructs were subcloned to expression vector pGO, containing $E.\ coli$ GAP promoter and OmpA signal peptide sequence for periplasmatic localization of the target protein. The sequence encoding the four domains was prepared by amplifying with oligonucleotides containing the restriction enzyme recognition sites for FspI and PstI on the 5' side and 3' side, respectively. The prepared DNA fragment encoding each domain was digested with FspI and PstI (New England Biolabs). Separately, expression vector was prepared with digestion with FspI and PstI and purified by agarose gel electrophoresis and recovered. Both were mixed and ligated with Quick ligation kit (New England Biolabs). The ligated plasmid expressing each domain was transformed into a chemical competent $E.\ coli$ K12 strain with a heat shock method.

Further mutations of amino acids N10, N45, Q19, and N60 in domain 3 were prepared in expression vector pJexpress401 (DNA2.0) containing T5 promoter under a lac operon control mechanism (SEQ ID NO: 7-11,13-14). Constructs were designed with and without OmpA signal peptide but without a C-terminal cysteine.

Tetramers of domain 3, dimer, tetramer and hexamer of domain 3 with N45, N10 and N60 mutations were also prepared in pJexpress401, with and without C-terminal cysteine (SEQ ID NO: 15-18).

Construct Expression and Purification

The $E.\ coli$ K12 recombinant cells were cultured in shake flasks with LB-broth (10 g peptone, 5 g yeast extract, 5 g NaCl) supplemented with 25 mg/l kanamycin at 37° C. until optical density at 600 nm reached 0.8. At this point protein expression was induced with Isopropyl β-D-1-thiogalacto-pyranoside (VWR International) with final concentration of 1 mM. Upon induction the temperature was lowered to 30° C. and the cultures were incubated for 5 hours. The cultivation was stopped and cells were centrifuged for 15 minutes at 4000×g and the supernatant was discarded. Cells were resuspended in 1/10 of culturing volume with phosphate buffered saline (PBS) and sonicated using pulse-sonication with an active time of 2 minutes. The sonicated samples were clarified from cell debris by centrifugation at 6000×g for 30 minutes, followed by microfiltration with a membrane having a 0.2 μm pore size.

The purified ligands were analyzed with LC-MS to determine the purity and to ascertain that the molecular weight corresponded to the expected (based on the amino acid sequence).

Example 1

Figure 3:
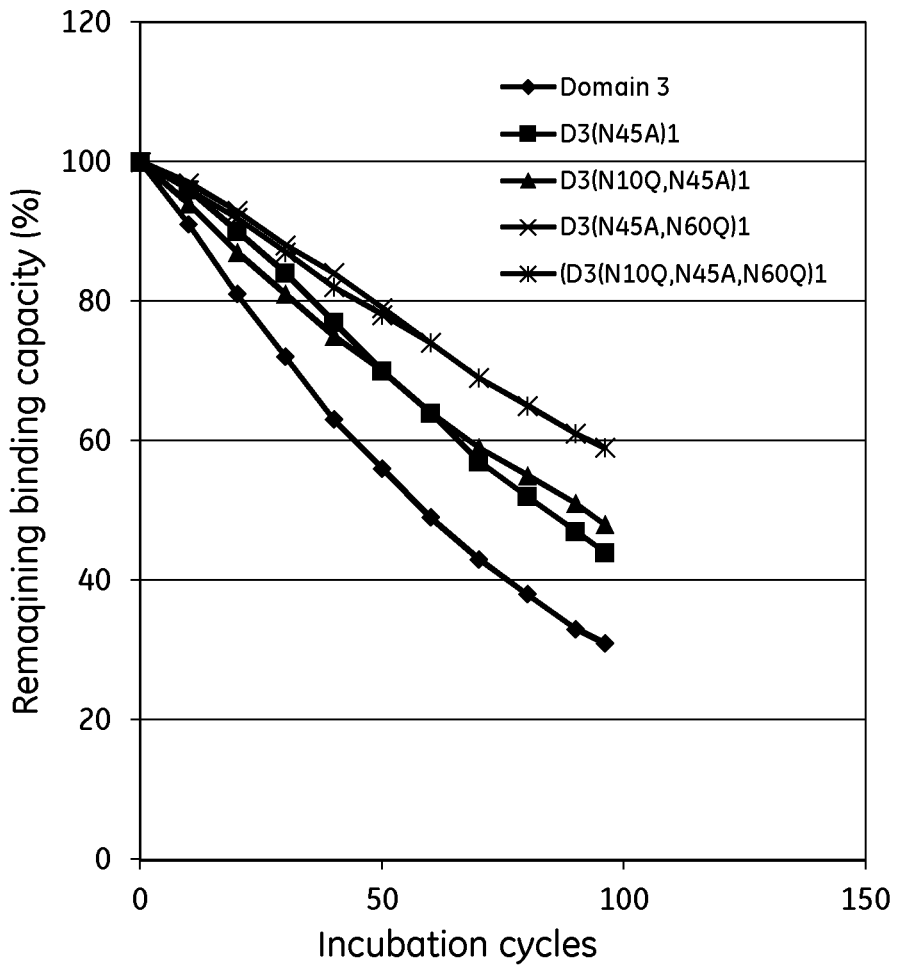
FIG. 3 shows the alkali stability of mutated kappa light chain-binding domains of Protein L.

The purified monomeric ligands listed in Table 1, further comprising, in the cases of the non-mutated single domains, a cysteine at the C terminus and an AQV sequence at the N-terminus, were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 1000RU in a Biacore instrument (GE Healthcare, Sweden). To follow the IgG binding capacity of the immobilized surface 1 mg/ml human polyclonal IgG (Gammanorm) was flowed over the chip and the signal strength was noted. The surface was then cleaned-in-place (CIP), i.e. flushed with 100 mM NaOH for 10 minutes at room temperature (22+/−2° C.). This was repeated for 96 cycles and the immobilized ligand alkaline stability was followed as the relative loss of IgG binding capacity (signal strength) after each cycle. The results for the non-mutated domains are shown in FIG. 2 and indicate that Domain 1 has a distinctly lower alkali stability than the other domains and that Domain 3 has the highest alkali stability. Results for single-domain asparagine mutants of Domain 3 are shown in FIG. 3 and show an improved alkali stability for all the mutants in comparison with the parental Domain 3, which was used as a reference in parallel with the mutations.

TABLE 1

| Ligand | Sequence | Retained capacity after 96 cycles (%) | Ref. capacity (%) | Sample/ref. ratio |
|---|---|---|---|---|
| Domain 1 (D1) | SEQ ID NO: 2 | 13 | 31 | 0.42 |
| Domain 2 (D2) | SEQ ID NO: 12 | 22 | 31 | 0.71 |
| Domain 3 (D3) | SEQ ID NO: 4 | 31 | 31 | 1.00 |
| Domain 4 (D4) | SEQ ID NO: 5 | 26 | 31 | 0.84 |
| D3(N45A)1 | SEQ ID NO: 7 | 44 | 31 | 1.42 |
| D3(N10Q, N45A)1 | SEQ ID NO: 8 | 48 | 31 | 1.55 |
| D3(N45A, N60Q)1 | SEQ ID NO: 9 | 59 | 31 | 1.90 |
| D3(N10Q, N45A, N60Q)1 | SEQ ID NO: 11 | 59 | 31 | 1.90 |
| Domain 3 (D3) | SEQ ID NO: 4 | 28 | 28 | 1.00 |
| D3(Q19A)1 | SEQ ID NO: 13 | 28 | 28 | 1.00 |
| D3(Q19E)1 | SEQ ID NO: 14 | 31 | 28 | 1.11 |

Example 2

Figure 4:
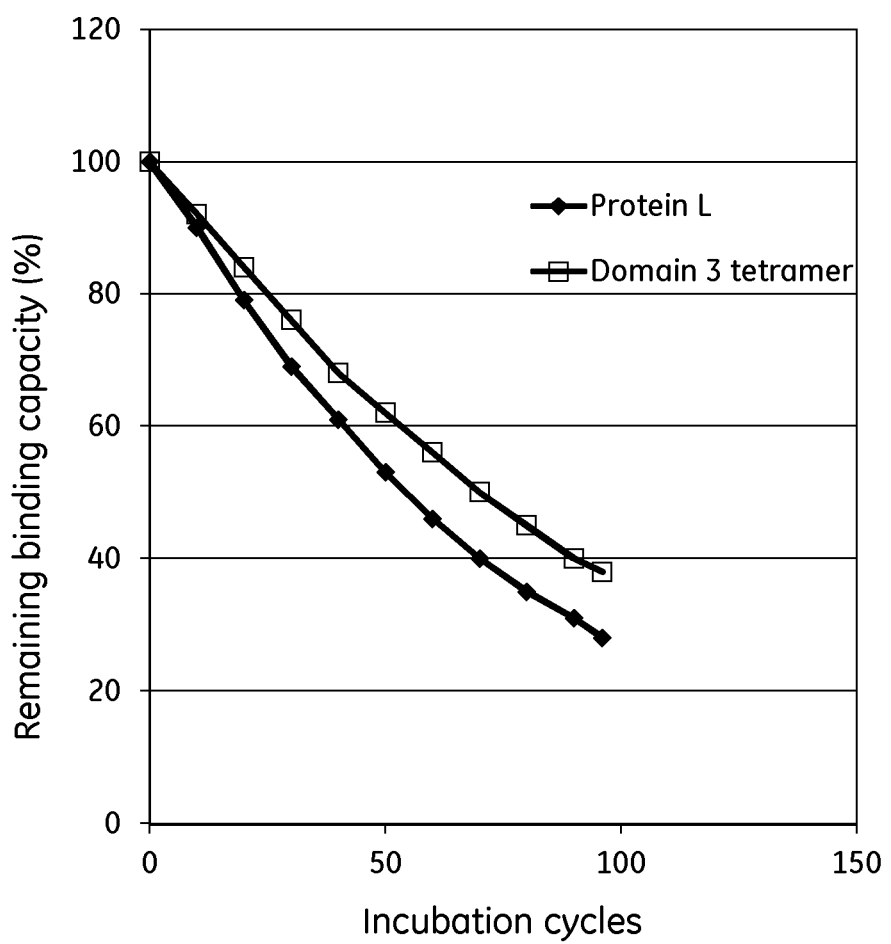
FIG. 4 shows the alkali stability of Protein L ligands comprising four domains.

The purified multidomain ligands listed in Table 2 were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 1000 RU in a Biacore instrument (GE Healthcare, Sweden). The Protein L had an additional AIH-NRA sequence at the N-terminus. To follow the IgG binding capacity of the immobilized surface 1 mg/ml human polyclonal IgG (Gammanorm) was flowed over the chip and the signal strength was noted. The surface was then cleaned-in-place (CIP), i.e. flushed with 100 mM NaOH for 10 minutes at room temperature (22+/−2° C.). This was repeated for 96 cycles and the immobilized ligand alkaline stability was followed as the relative loss of IgG binding capacity (signal strength) after each cycle. The results are shown in Table 2 and FIG. 4 and show that the tetrameric Domain 3 has an improved alkali stability in comparison with Protein L which was run in parallel as a reference.

TABLE 2

| Ligand | Sequence | Retained capacity after 96 cycles (%) | Ref. capacity (%) | Sample/ref. ratio |
|---|---|---|---|---|
| Protein L | SEQ ID NO: 1 | 28 | 28 | 1.00 |
| Domain 3 tetramer | SEQ ID NO: 15 | 38 | 28 | 1.36 |

Example 3

Figure 5:
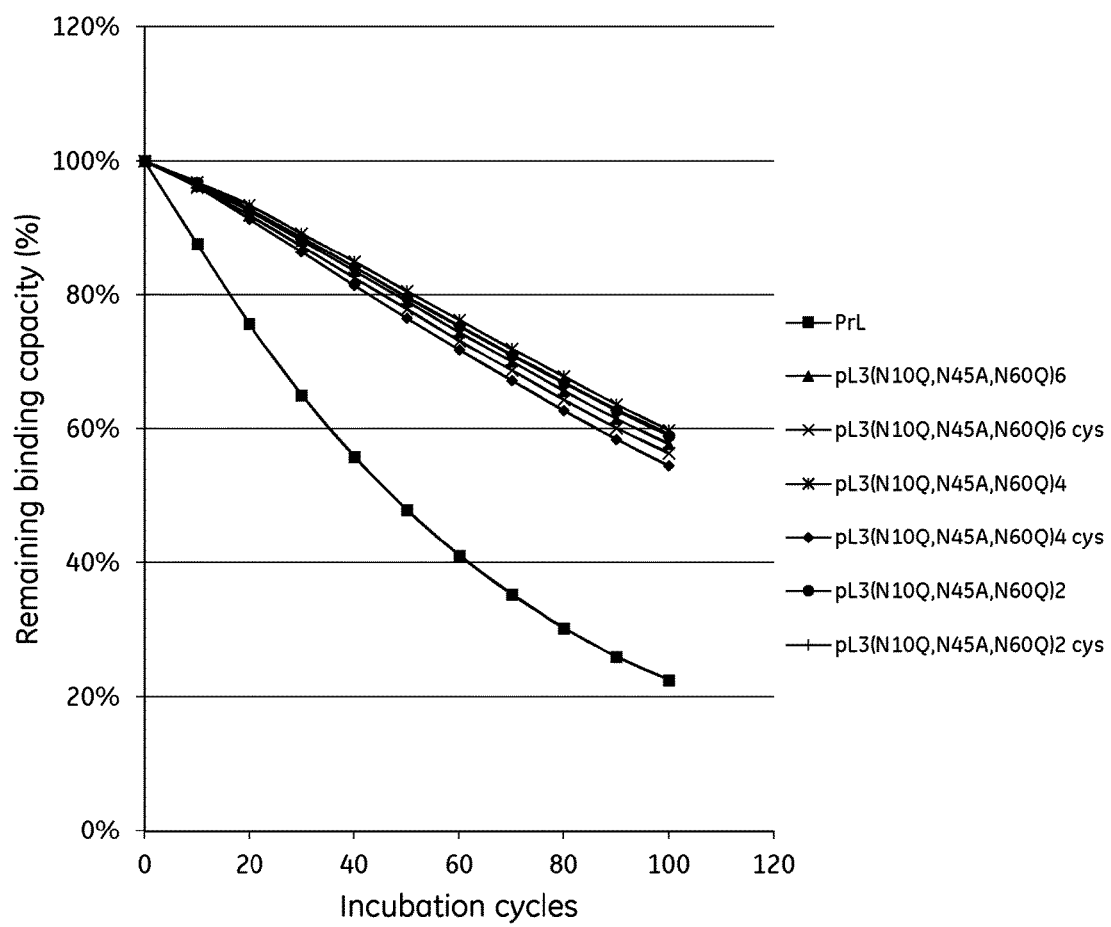
FIG. 5 shows the alkali stability of mutated dimeric, tetrameric and hexameric kappa light chain-binding domains of Protein L in comparison with Protein L.

The purified multidomain ligands listed in Table 3 were immobilized on Biacore CM5 sensor chips and evaluated by the methods used in Example 2. –cys at the end of the ligand designation indicates that the ligand has a C-terminal cysteine in addition to the sequence defined by SEQ ID NO: 16-18. The results are shown in Table 3 and FIG. 5 and show that all the mutated Domain 3 dimers, tetramers and hexamers have an improved alkali stability in comparison with Protein L which was run in parallel as a reference.

TABLE 3

| Ligand | Sequence | Retained capacity after 100 cycles (%) | Ref. capacity (%) | Sample/ref. ratio |
|---|---|---|---|---|
| Protein L | SEQ ID NO: 1 | 23 | 23 | 1.00 |
| D3(N10Q, N45A, N60Q)2 | SEQ ID NO: 16 | 59 | 23 | 2.56 |
| D3(N10Q, N45A, N60Q)2-cys | SEQ ID NO: 16 | 59 | 23 | 2.56 |
| D3(N10Q, N45A, N60Q)4 | SEQ ID NO: 17 | 60 | 23 | 2.61 |
| D3(N10Q, N45A, N60Q)4-cys | SEQ ID NO: 17 | 54 | 23 | 2.35 |
| D3(N10Q, N45A, N60Q)6 | SEQ ID NO: 18 | 58 | 23 | 2.52 |
| D3(N10Q, N45A, N60Q)6-cys | SEQ ID NO: 18 | 56 | 23 | 2.43 |

Example 4

The purified di-, tetra- and hexameric ligands of Table 4 were immobilized on agarose beads using the methods described below and assessed for capacity. The results are shown in Table 4.

TABLE 4

| Ligand | Sequence | Ligand content | QB10 Fab mg/ml | QB10 Dab mg/ml |
|---|---|---|---|---|
| D3(N10Q, N45A, N60Q)2 | SEQ ID NO: 16 | 9.5 mg/ml | 19.3 | 15.4 |
| D3(N10Q, N45A, N60Q)4 | SEQ ID NO: 17 | 8.8 mg/ml | 19.3 | 15.9 |
| D3(N10Q, N45A, N60Q)6 | SEQ ID NO: 18 | 11.0 mg/ml | 21.1 | 16.7 |

Activation

The base matrix used was rigid cross-linked agarose beads of 85 micrometers (volume-weighted) median diameter, prepared according to the methods of U.S. Pat. No. 6,602,990 and with a pore size corresponding to an inverse gel filtration chromatography Kay value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

The activated gel was washed with 5 GV 0.2 M phosphate/1 mM EDTA pH 11.5 (coupling buffer). 15 ml gel+13 mg ligand/ml gel (5.0 ml)+5.5 ml coupling buffer+4.7 g sodium sulfate were mixed in a 50 ml flask and stirred at 30° C. for 18.5 h. The pH was measured as 10.8.

After immobilization the gels were washed 3×GV with distilled water and then 5×GV with 0.1 M phosphate/1 mM EDTA pH 8.5. The gels+1 GV {0.1 M phosphate/1 mM EDTA/7.5% thioglycerol pH 8.5} was mixed and the flask was stirred at 45° C. for 2 h 20 min. The gel was then washed alternately with 1×GV 0.1 M HAc and 1×GV {0.1 M TRIS/0.15 M NaCl pH 8.5} and and then 6×GV with distilled water. Gel samples were sent to an external laboratory for amino acid analysis and the ligand content (mg/ml gel) was calculated from the total amino acid content. The coupling protocol used provides multipoint coupling, with several lysines of each domain attached to the gel.

2 ml of resin was packed in TRICORN™ 5 100 columns.

Protein a) Purified Fab prepared from a papain-digested IgG mAb, diluted to 1 mg/ml in Equilibration buffer.

b) Purified Dab prepared from heat-treated *E. coli* supernatant, diluted to 1 mg/ml in Equilibration buffer. The Dab contained solely a kappa light chain, without any antigen-binding site.

Equilibration Buffer

APB Phosphate buffer 20 mM+0.15 M NaCl, pH 7,4 (Medicago)

Adsorption Buffer

APB Phosphate buffer 20 mM+0.15 M NaCl, pH 7.4 (Medicago).

Elution Buffer 25 mM citrate pH 2.5

The breakthrough capacity was determined with an ÄKTAExplorer 10 system at a residence time of 4 minutes. Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with equilibration buffer and eluted at pH 2.5 at a flow rate of 0.5 ml/min.

For calculation of breakthrough capacity at 10%, the equation below was used. That is the amount of Fab/Dab that is loaded onto the column until the concentration of Fab/Dab in the column effluent is 10% of the Fab/Dab concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding proteins;
$A(V)$=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated and the appearance of the curve was studied. The curve was also studied regarding binding, elution and CIP peak. The dynamic binding capacity (DBC) was calculated for 10 and 80% breakthrough.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. A polypeptide comprising the amino acid sequence selected from the group consisting of sequences defined by SEQ ID NOS: 15-18.

2. The polypeptide of claim 1, further comprising at the C-terminus or N-terminus one or more coupling elements, selected from the group consisting of a cysteine residue, a plurality of lysine residues and a plurality of histidine residues.

3. The polypeptide of claim 1, further comprising an N-terminal moiety.

4. The polypeptide of claim 1, further comprising a C-terminal moiety.

5. A nucleic acid or a vector encoding a polypeptide according to claim 1.

6. An expression system, which comprises a nucleic acid or vector according to claim 5.

7. A separation matrix, wherein a plurality of polypeptides or multimers of claim 1 have been coupled to a solid support.

8. The separation matrix according to claim 7, wherein the polypeptides or multimers have been coupled to the solid support by multipoint attachment.

9. The separation matrix according to claim 7, wherein the solid support is a polysaccharide.

10. The polypeptide of claim 1, comprising the amino acid sequence defined by SEQ ID NO:15.

11. The polypeptide of claim 1, comprising the amino acid sequence defined by SEQ ID NO:16.

12. The polypeptide of claim 1, comprising the amino acid sequence defined by SEQ ID NO:17.

13. The polypeptide of claim 1, comprising the amino acid sequence defined by SEQ ID NO:18.

* * * * *

SEQUENCE LISTING

```
<160> NUMBER OF SEQ ID NOS: 18

<210> SEQ ID NO 1
<211> LENGTH: 301
<212> TYPE: PRT
<213> ORGANISM: Peptostreptococcus magnus

<400> SEQUENCE: 1

Lys Glu Glu Thr Pro Glu Thr Pro Glu Thr Asp Ser Glu Glu Glu Val
1               5                   10                  15

Thr Ile Lys Ala Asn Leu Ile Phe Ala Asn Gly Ser Thr Gln Thr Ala
            20                  25                  30

Glu Phe Lys Gly Thr Phe Glu Lys Ala Thr Ser Glu Ala Tyr Ala Tyr
        35                  40                  45

Ala Asp Thr Leu Lys Lys Asp Asn Gly Glu Tyr Thr Val Asp Val Ala
    50                  55                  60
```

```
Asp Lys Gly Tyr Thr Leu Asn Ile Lys Phe Ala Gly Lys Glu Lys Thr
 65                  70                  75                  80

Pro Glu Glu Pro Lys Glu Glu Val Thr Ile Lys Ala Asn Leu Ile Tyr
                 85                  90                  95

Ala Asp Gly Lys Thr Gln Thr Ala Glu Phe Lys Gly Thr Phe Glu Glu
            100                 105                 110

Ala Thr Ala Glu Ala Tyr Arg Tyr Ala Asp Ala Leu Lys Lys Asp Asn
        115                 120                 125

Gly Glu Tyr Thr Val Asp Val Ala Asp Lys Gly Tyr Thr Leu Asn Ile
    130                 135                 140

Lys Phe Ala Gly Lys Glu Lys Thr Pro Glu Glu Pro Lys Glu Glu Val
145                 150                 155                 160

Thr Ile Lys Ala Asn Leu Ile Tyr Ala Asp Gly Lys Thr Gln Thr Ala
                165                 170                 175

Glu Phe Lys Gly Thr Phe Glu Glu Ala Thr Ala Glu Ala Tyr Arg Tyr
            180                 185                 190

Ala Asp Leu Leu Ala Lys Glu Asn Gly Lys Tyr Thr Val Asp Val Ala
        195                 200                 205

Asp Lys Gly Tyr Thr Leu Asn Ile Lys Phe Ala Gly Lys Glu Lys Thr
    210                 215                 220

Pro Glu Glu Pro Lys Glu Glu Val Thr Ile Lys Ala Asn Leu Ile Tyr
225                 230                 235                 240

Ala Asp Gly Lys Thr Gln Thr Ala Glu Phe Lys Gly Thr Phe Ala Glu
                245                 250                 255

Ala Thr Ala Glu Ala Tyr Arg Tyr Ala Asp Leu Leu Ala Lys Glu Asn
            260                 265                 270

Gly Lys Tyr Thr Ala Asp Leu Glu Asp Gly Gly Tyr Thr Ile Asn Ile
        275                 280                 285

Arg Phe Ala Gly Lys Lys Val Asp Glu Lys Pro Glu Glu
    290                 295                 300

<210> SEQ ID NO 2
<211> LENGTH: 72
<212> TYPE: PRT
<213> ORGANISM: Peptostreptococcus magnus

<400> SEQUENCE: 2

Ser Glu Glu Glu Val Thr Ile Lys Ala Asn Leu Ile Phe Ala Asn Gly
 1               5                  10                  15

Ser Thr Gln Thr Ala Glu Phe Lys Gly Thr Phe Glu Lys Ala Thr Ser
                20                  25                  30

Glu Ala Tyr Ala Tyr Ala Asp Thr Leu Lys Lys Asp Asn Gly Glu Tyr
            35                  40                  45

Thr Val Asp Val Ala Asp Lys Gly Tyr Thr Leu Asn Ile Lys Phe Ala
        50                  55                  60

Gly Lys Glu Lys Thr Pro Glu Glu
 65                 70

<210> SEQ ID NO 3
<211> LENGTH: 72
<212> TYPE: PRT
<213> ORGANISM: Peptostreptococcus magnus

<400> SEQUENCE: 3

Pro Lys Glu Glu Val Thr Ile Lys Ala Asn Leu Ile Tyr Ala Asp Gly
 1               5                  10                  15
```

```
Lys Thr Gln Thr Ala Glu Phe Lys Gly Thr Phe Glu Glu Ala Thr Ala
            20                  25                  30

Glu Ala Tyr Arg Tyr Ala Asp Ala Leu Lys Lys Asp Asn Gly Glu Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70
```

<210> SEQ ID NO 4
<211> LENGTH: 72
<212> TYPE: PRT
<213> ORGANISM: Peptostreptococcus magnus

<400> SEQUENCE: 4

```
Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Asn Gly Lys Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70
```

<210> SEQ ID NO 5
<211> LENGTH: 74
<212> TYPE: PRT
<213> ORGANISM: Peptostreptococcus magnus

<400> SEQUENCE: 5

```
Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Ala Glu Ala Thr Ala
            20                  25                  30

Glu Ala Tyr Arg Tyr Ala Asp Leu Leu Ala Lys Glu Asn Gly Lys Tyr
        35                  40                  45

Thr Ala Asp Leu Glu Asp Gly Gly Tyr Thr Ile Asn Ile Arg Phe Ala
    50                  55                  60

Gly Lys Lys Val Asp Glu Lys Pro Glu Glu
65                  70
```

<210> SEQ ID NO 6
<211> LENGTH: 65
<212> TYPE: PRT
<213> ORGANISM: Peptostreptococcus magnus

<400> SEQUENCE: 6

```
Glu Lys Glu Gln Val Thr Ile Lys Glu Asn Ile Tyr Phe Glu Asp Gly
1               5                   10                  15

Thr Val Gln Thr Ala Thr Phe Lys Gly Thr Phe Ala Glu Ala Thr Ala
            20                  25                  30

Glu Ala Tyr Arg Tyr Ala Asp Leu Leu Ser Lys Glu His Gly Lys Tyr
        35                  40                  45

Thr Ala Asp Leu Glu Asp Gly Gly Tyr Thr Ile Asn Ile Arg Phe Ala
    50                  55                  60

Gly
```

<210> SEQ ID NO 7
<211> LENGTH: 72
<212> TYPE: PRT
<213> ORGANISM: Escherichia coli

<400> SEQUENCE: 7

Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70

<210> SEQ ID NO 8
<211> LENGTH: 72
<212> TYPE: PRT
<213> ORGANISM: Escherichia coli

<400> SEQUENCE: 8

Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70

<210> SEQ ID NO 9
<211> LENGTH: 72
<212> TYPE: PRT
<213> ORGANISM: Escherichia coli

<400> SEQUENCE: 9

Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
        35                  40                  45

Thr Val Asp Val Ala Asp Lys Gly Tyr Thr Leu Gln Ile Lys Phe Ala
    50                  55                  60

Gly Lys Glu Lys Thr Pro Glu Glu
65                  70

<210> SEQ ID NO 10
<211> LENGTH: 72
<212> TYPE: PRT
<213> ORGANISM: Escherichia coli

<400> SEQUENCE: 10

```
Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Asn Gly Lys Tyr
        35                  40                  45

Thr Val Asp Val Ala Asp Lys Gly Tyr Thr Leu Gln Ile Lys Phe Ala
    50                  55                  60

Gly Lys Glu Lys Thr Pro Glu Glu
65                  70
```

<210> SEQ ID NO 11
<211> LENGTH: 72
<212> TYPE: PRT
<213> ORGANISM: Escherichia coli

<400> SEQUENCE: 11

```
Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
        35                  40                  45

Thr Val Asp Val Ala Asp Lys Gly Tyr Thr Leu Gln Ile Lys Phe Ala
    50                  55                  60

Gly Lys Glu Lys Thr Pro Glu Glu
65                  70
```

<210> SEQ ID NO 12
<211> LENGTH: 72
<212> TYPE: PRT
<213> ORGANISM: Escherichia coli

<400> SEQUENCE: 12

```
Pro Lys Glu Glu Val Thr Ile Lys Ala Asn Leu Ile Tyr Ala Asp Gly
1               5                   10                  15

Lys Thr Gln Thr Ala Glu Phe Lys Gly Thr Phe Glu Glu Ala Ala Ala
            20                  25                  30

Glu Ala Tyr Arg Tyr Ala Asp Ala Leu Lys Lys Asp Asn Gly Glu Tyr
        35                  40                  45

Thr Val Asp Val Ala Asp Lys Gly Tyr Thr Leu Asn Ile Lys Phe Ala
    50                  55                  60

Gly Lys Glu Lys Thr Pro Glu Glu
65                  70
```

<210> SEQ ID NO 13
<211> LENGTH: 72
<212> TYPE: PRT
<213> ORGANISM: Escherichia coli

<400> SEQUENCE: 13

```
Pro Lys Glu Glu Val Thr Ile Lys Ala Asn Leu Ile Tyr Ala Asp Gly
1               5                   10                  15

Lys Thr Ala Thr Ala Glu Phe Lys Gly Thr Phe Glu Glu Ala Thr Ala
            20                  25                  30

Glu Ala Tyr Arg Tyr Ala Asp Leu Leu Ala Lys Glu Asn Gly Lys Tyr
        35                  40                  45

Thr Val Asp Val Ala Asp Lys Gly Tyr Thr Leu Asn Ile Lys Phe Ala
```

50                  55                  60

Gly Lys Glu Lys Thr Pro Glu Glu
 65                  70

<210> SEQ ID NO 14
<211> LENGTH: 72
<212> TYPE: PRT
<213> ORGANISM: Escherichia coli

<400> SEQUENCE: 14

Pro Lys Glu Glu Val Thr Ile Lys Ala Asn Leu Ile Tyr Ala Asp Gly
 1               5                  10                  15

Lys Thr Glu Thr Ala Glu Phe Lys Gly Thr Phe Glu Glu Ala Thr Ala
                20                  25                  30

Glu Ala Tyr Arg Tyr Ala Asp Leu Leu Ala Lys Glu Asn Gly Lys Tyr
            35                  40                  45

Thr Val Asp Val Ala Asp Lys Gly Tyr Thr Leu Asn Ile Lys Phe Ala
        50                  55                  60

Gly Lys Glu Lys Thr Pro Glu Glu
 65                  70

<210> SEQ ID NO 15
<211> LENGTH: 288
<212> TYPE: PRT
<213> ORGANISM: Escherichia coli

<400> SEQUENCE: 15

Pro Lys Glu Glu Val Thr Ile Lys Ala Asn Leu Ile Tyr Ala Asp Gly
 1               5                  10                  15

Lys Thr Gln Thr Ala Glu Phe Lys Gly Thr Phe Glu Glu Ala Thr Ala
                20                  25                  30

Glu Ala Tyr Arg Tyr Ala Asp Leu Leu Ala Lys Glu Asn Gly Lys Tyr
            35                  40                  45

Thr Val Asp Val Ala Asp Lys Gly Tyr Thr Leu Asn Ile Lys Phe Ala
        50                  55                  60

Gly Lys Glu Lys Thr Pro Glu Glu Pro Lys Glu Glu Val Thr Ile Lys
 65                  70                  75                  80

Ala Asn Leu Ile Tyr Ala Asp Gly Lys Thr Gln Thr Ala Glu Phe Lys
                85                  90                  95

Gly Thr Phe Glu Glu Ala Thr Ala Glu Ala Tyr Arg Tyr Ala Asp Leu
                100                 105                 110

Leu Ala Lys Glu Asn Gly Lys Tyr Thr Val Asp Val Ala Asp Lys Gly
            115                 120                 125

Tyr Thr Leu Asn Ile Lys Phe Ala Gly Lys Glu Lys Thr Pro Glu Glu
        130                 135                 140

Pro Lys Glu Glu Val Thr Ile Lys Ala Asn Leu Ile Tyr Ala Asp Gly
145                 150                 155                 160

Lys Thr Gln Thr Ala Glu Phe Lys Gly Thr Phe Glu Glu Ala Thr Ala
                165                 170                 175

Glu Ala Tyr Arg Tyr Ala Asp Leu Leu Ala Lys Glu Asn Gly Lys Tyr
            180                 185                 190

Thr Val Asp Val Ala Asp Lys Gly Tyr Thr Leu Asn Ile Lys Phe Ala
        195                 200                 205

Gly Lys Glu Lys Thr Pro Glu Glu Pro Lys Glu Glu Val Thr Ile Lys
    210                 215                 220

Ala Asn Leu Ile Tyr Ala Asp Gly Lys Thr Gln Thr Ala Glu Phe Lys

```
                225                 230                 235                 240
Gly Thr Phe Glu Glu Ala Thr Ala Glu Ala Tyr Arg Tyr Ala Asp Leu
                        245                 250                 255

Leu Ala Lys Glu Asn Gly Lys Tyr Thr Val Asp Val Ala Asp Lys Gly
                260                 265                 270

Tyr Thr Leu Asn Ile Lys Phe Ala Gly Lys Glu Lys Thr Pro Glu Glu
                275                 280                 285
```

<210> SEQ ID NO 16
<211> LENGTH: 144
<212> TYPE: PRT
<213> ORGANISM: Escherichia coli

<400> SEQUENCE: 16

```
Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
                20                  25                  30

Glu Ala Tyr Arg Tyr Ala Asp Leu Leu Ala Lys Glu Ala Gly Lys Tyr
                35                  40                  45

Thr Val Asp Val Ala Asp Lys Gly Tyr Thr Leu Gln Ile Lys Phe Ala
            50                  55                  60

Gly Lys Glu Lys Thr Pro Glu Glu Pro Lys Glu Glu Val Thr Ile Lys
65                  70                  75                  80

Ala Gln Leu Ile Tyr Ala Asp Gly Lys Thr Gln Thr Ala Glu Phe Lys
                85                  90                  95

Gly Thr Phe Glu Glu Ala Thr Ala Glu Ala Tyr Arg Tyr Ala Asp Leu
                100                 105                 110

Leu Ala Lys Glu Ala Gly Lys Tyr Thr Val Asp Val Ala Asp Lys Gly
                115                 120                 125

Tyr Thr Leu Gln Ile Lys Phe Ala Gly Lys Glu Lys Thr Pro Glu Glu
                130                 135                 140
```

<210> SEQ ID NO 17
<211> LENGTH: 288
<212> TYPE: PRT
<213> ORGANISM: Escherichia coli

<400> SEQUENCE: 17

```
Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
                20                  25                  30

Glu Ala Tyr Arg Tyr Ala Asp Leu Leu Ala Lys Glu Ala Gly Lys Tyr
                35                  40                  45

Thr Val Asp Val Ala Asp Lys Gly Tyr Thr Leu Gln Ile Lys Phe Ala
            50                  55                  60

Gly Lys Glu Lys Thr Pro Glu Glu Pro Lys Glu Glu Val Thr Ile Lys
65                  70                  75                  80

Ala Gln Leu Ile Tyr Ala Asp Gly Lys Thr Gln Thr Ala Glu Phe Lys
                85                  90                  95

Gly Thr Phe Glu Glu Ala Thr Ala Glu Ala Tyr Arg Tyr Ala Asp Leu
                100                 105                 110

Leu Ala Lys Glu Ala Gly Lys Tyr Thr Val Asp Val Ala Asp Lys Gly
                115                 120                 125

Tyr Thr Leu Gln Ile Lys Phe Ala Gly Lys Glu Lys Thr Pro Glu Glu
```

```
                130                 135                 140
Pro Lys Glu Glu Val Thr Ile Lys Ala Gln Leu Ile Tyr Ala Asp Gly
145                 150                 155                 160

Lys Thr Gln Thr Ala Glu Phe Lys Gly Thr Phe Glu Ala Thr Ala
                165                 170                 175

Glu Ala Tyr Arg Tyr Ala Asp Leu Leu Ala Lys Glu Ala Gly Lys Tyr
                180                 185                 190

Thr Val Asp Val Ala Asp Lys Gly Tyr Thr Leu Gln Ile Lys Phe Ala
                195                 200                 205

Gly Lys Glu Lys Thr Pro Glu Glu Pro Lys Glu Glu Val Thr Ile Lys
            210                 215                 220

Ala Gln Leu Ile Tyr Ala Asp Gly Lys Thr Gln Thr Ala Glu Phe Lys
225                 230                 235                 240

Gly Thr Phe Glu Glu Ala Thr Ala Glu Ala Tyr Arg Tyr Ala Asp Leu
                245                 250                 255

Leu Ala Lys Glu Ala Gly Lys Tyr Thr Val Asp Val Ala Asp Lys Gly
            260                 265                 270

Tyr Thr Leu Gln Ile Lys Phe Ala Gly Lys Glu Lys Thr Pro Glu Glu
            275                 280                 285

<210> SEQ ID NO 18
<211> LENGTH: 432
<212> TYPE: PRT
<213> ORGANISM: Escherichia coli

<400> SEQUENCE: 18

Pro Lys Glu Glu Val Thr Ile Lys Ala Gln Leu Ile Tyr Ala Asp Gly
1               5                   10                  15

Lys Thr Gln Thr Ala Glu Phe Lys Gly Thr Phe Glu Glu Ala Thr Ala
            20                  25                  30

Glu Ala Tyr Arg Tyr Ala Asp Leu Leu Ala Lys Glu Ala Gly Lys Tyr
            35                  40                  45

Thr Val Asp Val Ala Asp Lys Gly Tyr Thr Leu Gln Ile Lys Phe Ala
        50                  55                  60

Gly Lys Glu Lys Thr Pro Glu Glu Pro Lys Glu Glu Val Thr Ile Lys
65                  70                  75                  80

Ala Gln Leu Ile Tyr Ala Asp Gly Lys Thr Gln Thr Ala Glu Phe Lys
                85                  90                  95

Gly Thr Phe Glu Glu Ala Thr Ala Glu Ala Tyr Arg Tyr Ala Asp Leu
            100                 105                 110

Leu Ala Lys Glu Ala Gly Lys Tyr Thr Val Asp Val Ala Asp Lys Gly
        115                 120                 125

Tyr Thr Leu Gln Ile Lys Phe Ala Gly Lys Glu Lys Thr Pro Glu Glu
    130                 135                 140

Pro Lys Glu Glu Val Thr Ile Lys Ala Gln Leu Ile Tyr Ala Asp Gly
145                 150                 155                 160

Lys Thr Gln Thr Ala Glu Phe Lys Gly Thr Phe Glu Glu Ala Thr Ala
                165                 170                 175

Glu Ala Tyr Arg Tyr Ala Asp Leu Leu Ala Lys Glu Ala Gly Lys Tyr
            180                 185                 190

Thr Val Asp Val Ala Asp Lys Gly Tyr Thr Leu Gln Ile Lys Phe Ala
        195                 200                 205

Gly Lys Glu Lys Thr Pro Glu Glu Pro Lys Glu Glu Val Thr Ile Lys
    210                 215                 220
```

```
Ala Gln Leu Ile Tyr Ala Asp Gly Lys Thr Gln Thr Ala Glu Phe Lys
225                 230                 235                 240

Gly Thr Phe Glu Glu Ala Thr Ala Glu Ala Tyr Arg Tyr Ala Asp Leu
                245                 250                 255

Leu Ala Lys Glu Ala Gly Lys Tyr Thr Val Asp Val Ala Asp Lys Gly
                260                 265                 270

Tyr Thr Leu Gln Ile Lys Phe Ala Gly Lys Glu Lys Thr Pro Glu Glu
            275                 280                 285

Pro Lys Glu Glu Val Thr Ile Lys Ala Gln Leu Ile Tyr Ala Asp Gly
        290                 295                 300

Lys Thr Gln Thr Ala Glu Phe Lys Gly Thr Phe Glu Glu Ala Thr Ala
305                 310                 315                 320

Glu Ala Tyr Arg Tyr Ala Asp Leu Leu Ala Lys Glu Ala Gly Lys Tyr
                325                 330                 335

Thr Val Asp Val Ala Asp Lys Gly Tyr Thr Leu Gln Ile Lys Phe Ala
                340                 345                 350

Gly Lys Glu Lys Thr Pro Glu Glu Pro Lys Glu Glu Val Thr Ile Lys
                355                 360                 365

Ala Gln Leu Ile Tyr Ala Asp Gly Lys Thr Gln Thr Ala Glu Phe Lys
    370                 375                 380

Gly Thr Phe Glu Glu Ala Thr Ala Glu Ala Tyr Arg Tyr Ala Asp Leu
385                 390                 395                 400

Leu Ala Lys Glu Ala Gly Lys Tyr Thr Val Asp Val Ala Asp Lys Gly
                405                 410                 415

Tyr Thr Leu Gln Ile Lys Phe Ala Gly Lys Glu Lys Thr Pro Glu Glu
            420                 425                 430
```